(12) United States Patent
Shiomi et al.

(10) Patent No.: US 11,542,222 B2
(45) Date of Patent: Jan. 3, 2023

(54) METHOD FOR PREPARING DICYANOALKANE AND BIS(AMINOMETHYL) ALKANE

(71) Applicant: MITSUBISHI GAS CHEMICAL COMPANY, INC., Chiyoda-ku (JP)

(72) Inventors: Noriyuki Shiomi, Niigata (JP); Emi Nakano, Niigata (JP); Akifumi Iida, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 17/045,897

(22) PCT Filed: Apr. 11, 2019

(86) PCT No.: PCT/JP2019/015738
§ 371 (c)(1),
(2) Date: Oct. 7, 2020

(87) PCT Pub. No.: WO2019/198782
PCT Pub. Date: Oct. 17, 2019

(65) Prior Publication Data
US 2021/0139408 A1 May 13, 2021

(30) Foreign Application Priority Data

Apr. 11, 2018 (JP) .............................. JP2018-076239

(51) Int. Cl.
*C07C 209/48* (2006.01)
*B01J 23/06* (2006.01)
(Continued)

(52) U.S. Cl.
CPC ............ *C07C 209/48* (2013.01); *B01J 23/06* (2013.01); *B01J 23/745* (2013.01); *B01J 25/00* (2013.01); *C07C 253/22* (2013.01)

(58) Field of Classification Search
None
See application file for complete search history.

(56) References Cited

U.S. PATENT DOCUMENTS

| 3,454,619 A | 7/1969 | Hayes |
| 2009/0054677 A1* | 2/2009 | Fukushima ........... C07C 211/21 558/311 |

(Continued)

FOREIGN PATENT DOCUMENTS

| EP | 0 232 712 A1 | 8/1987 |
| JP | 55-104242 A | 8/1980 |

(Continued)

OTHER PUBLICATIONS

"Heteroatom" (Illustrated Glossary of Organic Chemistry, downloaded from http://www.chem.ucla.edu/~harding/IGOC/H/heteroatom.html, on Mar. 15, 2022) (Year: 2022).*

(Continued)

*Primary Examiner* — Amy C Bonaparte
(74) *Attorney, Agent, or Firm* — Oblon, McClelland, Maier & Neustadt, L.L.P.

(57) ABSTRACT

A method for preparing a dicyanoalkane may omit a filtration for a catalyst after a cyanation reaction can by carrying out the cyanation reaction in a state in which precipitation of a metal catalyst is suppressed. A method for preparing a dicyanoalkane may involve cyanating one or more aliphatic dicarboxylic acids and/or salt(s) thereof with an ammonia source in the presence of a predetermined compound and a catalyst, wherein, in the cyanation, the amount of the predetermined compound is maintained at a predetermined amount or more with respect to the catalyst.

20 Claims, 2 Drawing Sheets

(51) Int. Cl.
   *B01J 23/745* (2006.01)
   *B01J 25/00* (2006.01)
   *C07C 253/22* (2006.01)

(56) References Cited

U.S. PATENT DOCUMENTS

| | | | |
|---|---|---|---|
| 2011/0190541 A1* | 8/2011 | Beillon | C07C 253/22 |
| | | | 564/491 |
| 2013/0144028 A1 | 6/2013 | Fruchey et al. | |
| 2013/0197269 A1 | 8/2013 | Yoshimura et al. | |
| 2013/0197270 A1 | 8/2013 | Yoshimura et al. | |
| 2016/0207875 A1 | 7/2016 | Fukuda et al. | |
| 2019/0225572 A1 | 7/2019 | Iida et al. | |
| 2020/0165195 A1* | 5/2020 | Iida | C07C 255/46 |
| 2020/0392072 A1* | 12/2020 | Nakano | C07C 253/22 |

FOREIGN PATENT DOCUMENTS

| | | |
|---|---|---|
| JP | 62-167749 A | 7/1987 |
| JP | 6078158 B2 | 2/2017 |
| WO | WO 2011/146440 A1 | 11/2011 |
| WO | WO 2012/046781 A1 | 4/2012 |
| WO | WO 2012/046782 A1 | 4/2012 |
| WO | WO 2015/016148 A1 | 2/2015 |
| WO | WO 2018/066447 A1 | 4/2018 |
| WO | WO 2019/035381 A1 | 2/2019 |

OTHER PUBLICATIONS

"Quantify" Dictionary.com, downloaded from https://www.dictionary.com/browse/quantify on Mar. 15, 2022 (Year: 2022).*

"Quantify" Cambridge online dictionary, downloaded from https://dictionary.cambridge.org/us/dictionary/english/quantify on Mar. 15, 2022 (Year: 2022).*

"Quantify" Merriam-Webster online dictionary, downloaded from https://www.merriam-webster.com/dictionary/quantify on Mar. 15, 2022 (Year: 2022).*

International Search Report dated Jul. 2, 2019 in PCT/JP2019/015738 filed on Apr. 11, 2019, citing documents AA-AE and AN-AV therein, 2 pages.

* cited by examiner

METHOD FOR PREPARING DICYANOALKANE AND BIS(AMINOMETHYL) ALKANE

TECHNICAL FIELD

The present invention relates to a method for producing dicyanoalkane and bis(aminomethyl)alkane.

BACKGROUND ART

Dicyanoalkane can be used as a raw material for obtaining bis(aminomethyl)alkane via hydrogenation. Since bis(aminomethyl)alkane is useful as a raw material of a resin, there is a need for a method for efficiently producing dicyanoalkane.

A step preceding the production from dicyanoalkane to bis(aminomethyl)alkane comprises a step of cyanating an alkane dicarboxylic acid. For this cyanation step, reaction using a metal catalyst is generally known. For example, Patent document 1 describes a method for producing trans-bis(aminomethyl)cyclohexane, wherein 1,4-dicyanocyclohexane is obtained from 1,4-cyclohexane dicarboxylic acid in the presence of a tin(II) oxide catalyst (Patent document 1, Example 1).

PRIOR ART DOCUMENT

Patent Document

Patent document 1: Japanese Patent No. 6078158

SUMMARY OF INVENTION

Problem to be Solved by the Invention

The method of Patent document 1, however, comprises a filtration step after the cyanation step to remove the solid matters (namely, the precipitated catalyst), and therefore there is still room for improvement.

The present invention was made under such circumstances and provides a novel method for producing dicyanoalkane, in which a step for filtrating the catalyst after the cyanation step can be omitted by carrying out cyanation while suppressing precipitation of the metal catalyst. Furthermore, according to the present invention, clogging risks of the transfer line and the distillation column by the precipitated catalyst can also be avoided.

Means for Solving the Problem

The present inventors have gone through intensive investigation to achieve the above-described objectives, and as a result of which found that precipitation of the catalyst can be suppressed by maintaining the amount of a specific compound at a predetermined level or more relative the catalyst during the cyanation step, thereby accomplishing the present invention.

Thus, the present invention is as follows.
[1] A method for producing dicyanoalkane, comprising a cyanation step, wherein, in the cyanation step, one or more kinds selected from the group consisting of aliphatic dicarboxylic acids and salts thereof are cyanated with an ammonia source in the presence of a metal oxide and/or a metal salt and an amide compound represented by General formula (1) below or a derivative thereof:

wherein, $R^1$ represents a substituted or unsubstituted hydrocarbon group,
wherein, in the cyanation step, the amount of the amide compound represented by General formula (1) above is maintained at 0.010 times equivalent or more to the total amount of the metal oxide and the metal salt.
[2] The method according to [1], wherein the ammonia source is obtained from ammonia, urea, ammonium hydrogen carbonate, ammonium carbonate or a heated concentrate of an aqueous ammonia solution of aliphatic dicarboxylic acid.
[3] The method according to [1] or [2], wherein the substituted or unsubstituted hydrocarbon group of $R^1$ is a monovalent group selected from the group consisting of a substituted or unsubstituted aliphatic hydrocarbon group, a substituted or unsubstituted alicyclic hydrocarbon group and a substituted or unsubstituted aromatic hydrocarbon group.
[4] The method according to any one of [1]-[3], wherein the amide compound represented by General formula (1) above is one or more kinds selected from the group consisting of carbamoyl alkane carboxylic acid, alkane diamide and cyanoalkane carboxamide.
[5] The method according to any one of [1]-[4], wherein the metal oxide is one or more kinds selected from the group consisting of zinc oxide, tin oxide and iron oxide.
[6] The method according to any one of [1]-[5], wherein the metal salt is one or more kinds selected from the group consisting of a carbonate, a carboxylate, a sulfate, a nitrate, a halide and a hydrate thereof.
[7] The method according to any one of [1]-[6], wherein the amount of the amide compound represented by General formula (1) above is maintained at 0.010 times equivalent or more to the total amount of the metal oxide and the metal salt by adding the amide compound represented by General formula (1) above or a derivative thereof during the cyanation step.
[8] The method according to any one of [1]-[7], wherein, in the cyanation step, the cyanation is ended before the amount of the amide compound represented by General formula (1) above becomes less than 0.010 times equivalent to the total amount of the metal oxide and the metal salt.
[9] The method according to any one of [1]-[8], wherein the amount of the amide compound represented by General formula (1) above is quantified in the cyanation step.
[10] A method for producing diaminoalkane, comprising an amination step, wherein, in the amination step, dicyanoalkane obtained by the method according to any one of [1]-[9] is hydrogenated to obtain bis(aminomethyl)alkane.

Effect of the Invention

The present invention can provide a novel method for producing dicyanoalkane, in which a step for filtrating the catalyst after the cyanation step can be omitted by carrying out cyanation while suppressing precipitation of the metal catalyst. In addition, according to the present invention, clogging risks of the transfer line and the distillation column caused by the precipitated catalyst can also be avoided.

MODES FOR CARRYING OUT THE INVENTION

Figure 1:
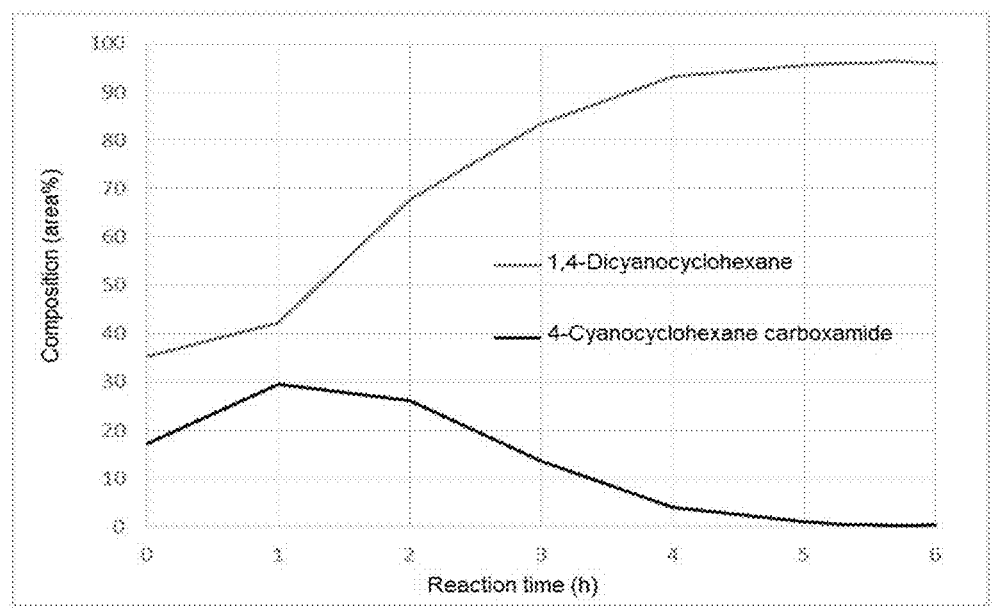
FIG. 1 shows results from the measurement of changes in the composition ratios of 1,4-dicyanocyclohexane and 4-cyanocyclohexane carboxamide by gas chromatography (hereinafter, also referred to as GC) before and after the precipitation of the catalyst.

Hereinafter, a mode for carrying out the present invention (hereinafter, also simply referred to as "this embodiment") will be described in detail, although the present invention should not be limited to the following embodiment. The present invention can be modified in various ways without departing from the scope of the invention.

1. Method for Producing Dicyanoalkane

A method for producing dicyanoalkane according to the present invention comprises a cyanation step (hereinafter, also referred to as a "cyanation step of the present invention") in which one or more kinds selected from the group consisting of aliphatic dicarboxylic acids and salts thereof are cyanated with an ammonia source in the presence of a metal oxide and/or a metal salt and an amide compound represented by General formula (1) below or a derivative thereof:

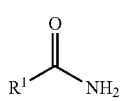

(1)

wherein, $R^1$ represents a substituted or unsubstituted hydrocarbon group, wherein, in the cyanation step, the amount of the amide compound represented by General formula (1) above is maintained at 0.010 times equivalent or more to the total amount of the metal oxide and the metal salt (hereinafter, also referred to as the "production method of the present invention"). Herein, unless otherwise specified, "equivalent" means "molar equivalent". Specifically, "0.010 times equivalent" means that the amount is 0.010 times in mole ratio.

Herein, dicyanoalkane is an alkane (also referred to as a saturated hydrocarbon or an aliphatic hydrocarbon) having two cyano groups (expressed as —CN and also referred to as nitrile groups), and may be either a chain alkane or a cyclic alkane. While the number of carbons of the alkane is not particularly limited, it is preferably 1-20, more preferably 4-10 and still more preferably 6-8 if it is a chain alkane, while preferably 3-8, more preferably 4-8 and still more preferably 5-6 if it is a cyclic alkane.

Dicyanoalkanes that can be produced by the production method of present invention comprise a variety of dicyanoalkanes. Examples of chain dicyanoalkanes include dicyanomethane, dicyanoethane, dicyanopropane, dicyanobutane, dicyanopentane, dicyanohexane, dicyanoheptane, dicyanooctane, dicyanononane and dicyanodecane. Among them, dicyanopentane, dicyanohexane and dicyanooctane are preferable, and 1,6-dicyanohexane (also referred to as suberonitrile) and 1,8-dicyanooctane (also referred to as sebaconitrile) are more preferable. Examples of cyclic dicyanoalkanes include dicyanocyclopropane, di cyanocyclobutane, dicyanocyclopentane, dicyanocyclohexane, dicyanocycloheptane, dicyanocyclooctane, dicyanocyclononane and dicyanocyclodecane. Among them, dicyanocyclopentane, dicyanocyclohexane and dicyanocycloheptane are preferable, and 1,2-dicyanocyclohexane, 1,3-dicyanocyclohexane and 1,4-dicyanocyclohexane are more preferable. Dicyanoalkane may further have one or more arbitrary substituents, where examples of such substituents include a halogen atom, a C1-C20 alkyl group and a C6-C12 aryl group.

According to the production method of the present invention, a dicyanoalkane can be obtained by cyanation of one or more kinds selected from the group consisting of aliphatic dicarboxylic acids and salts thereof. Such an aliphatic dicarboxylic acid comprises various aliphatic dicarboxylic acids. Examples of chain aliphatic dicarboxylic acids include methanedicarboxylic acid, ethanedicarboxylic acid, propanedicarboxylic acid, butanedicarboxylic acid, pentanedicarboxylic acid, hexanedicarboxylic acid, heptanedicarboxylic acid, octanedicarboxylic acid, nonanedicarboxylic acid and decanedicarboxylic acid. Among them, pentanedicarboxylic acid, hexanedicarboxylic acid and octanedicarboxylic acid are preferable, and 1,6-hexanedicarboxylic acid (suberic acid) and 1,8-octanedicarboxylic acid (sebacic acid) are more preferable. Examples of cyclic aliphatic dicarboxylic acids include cyclopropanedicarboxylic acid, cyclobutanedicarboxylic acid, cyclopentanedicarboxylic acid, cyclohexanedicarboxylic acid, cycloheptanedicarboxylic acid, cyclooctanedicarboxylic acid, cyclononanedicarboxylic acid and cyclodecanedicarboxylic acid. Among them, cyclopentanedicarboxylic acid, cyclohexanedicarboxylic acid and cycloheptanedicarboxylic acid are preferable, and 1,2-cyclohexanedicarboxylic acid, 1,3-cyclohexanedicarboxylic acid and 1,4-cyclohexanedicarboxylic acid are more preferable. Examples of a salt of an aliphatic dicarboxylic acid include ammonium salts and metal salts of aliphatic dicarboxylic acids. The aliphatic dicarboxylic acid may further have one or more arbitrary substituents, where examples of such substituents include a halogen atom, a C1-C20 alkyl group and a C6-C12 aryl group. In the cyanation step of the production method of the present invention, an aliphatic dicarboxylic acid used as a raw material may be produced by an ordinary method, or may be a commercially available product.

The flow of the cyanation step of the present invention will be described with reference to Scheme 1 below.

Scheme 1: Cyanation step

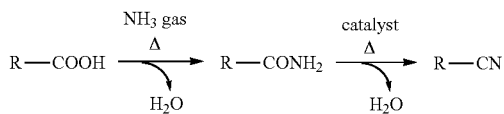

As shown in Scheme 1 above, reaction takes place between carboxylic acid as the starting material and ammonia gas, where carboxyl groups are sequentially converted into amide groups. These amide groups are dehydrated in the presence of a catalyst and converted into cyano groups, thereby obtaining nitrile as the compound of interest.

The cyanation step of the present invention is carried out in the presence of a metal oxide and/or a metal salt and an amide compound represented by General formula (1) below or a derivative thereof,

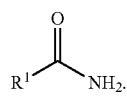

(1)

In the formula above, R¹ represents a substituted or unsubstituted hydrocarbon group. The substituted or unsubstituted hydrocarbon group of R¹ is preferably a monovalent group selected from the group consisting of a substituted or unsubstituted aliphatic hydrocarbon group, a substituted or unsubstituted alicyclic hydrocarbon group and a substituted or unsubstituted aromatic hydrocarbon group. Examples of such aliphatic hydrocarbon include methane, ethane, propane, butane, pentane, hexane, heptane, octane, nonane and decane. Among them, pentane, hexane and octane are favorable. Examples of the alicyclic hydrocarbon include cyclopropane, cyclobutane, cyclopentane, cyclohexane, cycloheptane, cyclooctane, cyclononane and cyclodecane. Examples of the aromatic hydrocarbon include benzene, pyrrole, furan, thiophene, pyridine, imidazole, pyrazole, oxazole and thiazole. Examples of the substituent include a cyano group, a nitro group, a carboxyl group, a halogen atom, a C1-C20 alkyl group and a C6-C12 aryl group.

Examples of the amide compound represented by General formula (1) above include one or more kinds selected from the group consisting of carbamoyl alkane carboxylic acid, alkane diamide and cyanoalkane carboxamide. Examples of a derivative of the amide compound represented by General formula (1) include those in which hydrogen of NH₂ of the amide compound represented by General formula (1) is substituted with other heteroatom. The amide compound represented by General formula (1) is preferably cyanoalkane carboxamide, and more preferably 4-cyanocyclohexane carboxamide, 7-cyanoheptaneamide or 9-cyanononaneamide.

According to the production method of the present invention, in the cyanation step, the amount of the amide compound represented by General formula (1) above is maintained at 0.010 times equivalent or more to the total amount of the metal oxide and the metal salt. Herein, the phrase "the amount of the amide compound represented by General formula (1) is maintained at 0.010 times equivalent or more to the total amount of the metal oxide and the metal salt" means that the amount of the amide compound represented by General formula (1) above becomes 0.010 times equivalent or more to the total amount of the metal oxide and the metal salt after the start of the reaction, and is then maintained at that amount. For example, if the amount of the amide compound represented by General formula (1) is less than 0.010 times equivalent to the total amount of the metal oxide and the metal salt immediately after the start of the reaction, then the phrase means to maintain the amount of the amide compound represented by General formula (1) once it has become 0.010 times equivalent or more. By maintaining the amount of the amide compound represented by General formula (1) at said amount or more, precipitation of the catalyst can be suppressed. Since the amount of the amide compound represented by General formula (1) may temporary be increased after the catalyst precipitation, the phrase "0.010 times equivalent" refers to the amount of the amide compound before precipitation of the catalyst.

Without wishing to be bound by any theory, the catalyst is considered to exist in a dissolved state once the carboxylic acid and a metal oxide or a metal salt as the cyanation catalyst, which are present in the reaction system, form a complex. It is also considered that since this complex of the carboxylic acid and the metal oxide or the metal salt as the cyanation catalyst can stably exist in the presence of a certain amount of the compound represented by General formula (1) above, the dissolved state of the catalyst can be maintained and thus precipitation of the catalyst can be suppressed effectively after the reaction. Formation of the complex can also be supported by the examples described herein. For example, as can be appreciated from FIG. 4 which shows the results from the LC-Mass analysis in Example 1, three molecules of 4-cyanocyclohexane carboxylic acid or a carboxylate ion thereof were confirmed to be connected to zinc oxide that was added as a catalyst to form a complex (considering that the detection took place in ESI negative ion mode, there is a possibility that 4-cyanocyclohexane carboxylic acid and/or a carboxylate ion thereof having less than three molecules may be forming a complex with zinc in the actual reaction solution). While whether or not precipitation of the catalyst is suppressed can be confirmed visually, it can also be confirmed by various analysis methods (for example, ICP analysis). When measured by ICP analysis, precipitation is considered to be sufficiently suppressed if the precipitated metal is 60 wt % or less relative to the metal contained in the added catalyst.

Herein, in a case of cyanation from 1,4-cyclohexanedicarboxylic acid to 1,4-dicyanocyclohexane, 4-cyanocyclohexane carboxylic acid, i.e., one of the carboxylic acids generated in the reaction system, forms a complex with zinc oxide, i.e., the catalyst, and that complex is considered to catalyze the reaction from 4-cyanocyclohexane carboxamide, i.e., one of the compounds represented by General formula (1) above, to 1,4-dicyanocyclohexane. And as the concentration of 4-cyanocyclohexane carboxamide in the system becomes low along with the reaction, it is considered that the chemical equilibrium shifts and degradation of the complex is promoted, leading to precipitation of the catalyst. Thus, for the first time, the present inventors found that precipitation of the catalyst can be suppressed by maintaining the amount of the compound represented by General formula (1) above at a predetermined level or higher. In addition, since precipitation of a catalyst can be suppressed by maintaining the chemical equilibrium, the compound represented by General formula (1) above does not necessarily have to be the reaction intermediate in the cyanation step. For example, while 4-cyanocyclohexane carboxamide, i.e., the compound represented by General formula (1) above, is an intermediate of the reaction that gives 1,4-dicyanocyclohexane from 1,4-cyclohexanedicarboxylic acid in the above example, a compound other than 4-cyanocyclohexane carboxamide may be used as the compound represented by General formula (1) above.

The amount of the amide compound represented by General formula (1) is 0.010 times equivalent or more, preferably 0.10 times equivalent or more and more preferably 0.50 times equivalent or more to the total amount of the metal oxide and the metal salt. The upper limit of the amount of the amide compound represented by General formula (1) is preferably 30 times equivalent or less and more preferably 25 times equivalent or less.

While the method for maintaining the amount of the amide compound represented by General formula (1) in the cyanation step of the present invention is not particularly limited, for example, an amide compound represented by General formula (1) or a derivative thereof may be added during the cyanation step.

Alternatively, the amount may be maintained by terminating the above-described cyanation before the amount of the amide compound represented by General formula (1) becomes less than 0.010 times equivalent to the total amount of the metal oxide and the metal salt in the cyanation step.

The amount of the amide compound represented by General formula (1) may be maintained by quantifying the amount of the amide compound represented by General formula (1) in the cyanation step, or by calculating and simulating the decrease rate of the amount of said compound in the cyanation step. For example, like Verification example 1 described hereinbelow, reaction can be proceeded until precipitation of the catalyst occurs for once so that change in the amount of the compound in the reaction system during that period can be recorded for simulation. In a preferred aspect of the present invention, the amount of the amide compound represented by General formula (1) is quantified in the cyanation step. By appropriately quantifying the amount during the reaction, the amount of the compound can be maintained more surely and thus suppressing precipitation of the catalyst more effectively. Herein, the amount of the amide compound represented by General formula (1) can be measured by gas chromatography, for example, gas chromatography described in Example 1. While the number and timing of the quantification are not particularly limited, quantification may take place, for example, every 10, 15, 20, 30, 40 or 50 minutes or every 1, 2, 3 or 4 hours. Moreover, the timing of the quantification may be altered during the reaction according to the progress of the reaction. For example, quantification may be conducted every 1 hour for the first 4 hours from the start of the reaction, and every 10 minutes thereafter.

Figure 4:
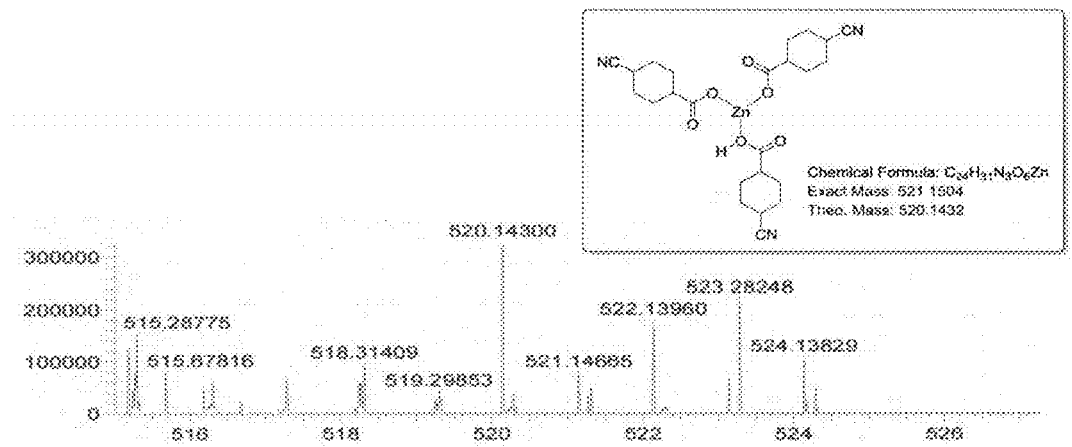
FIG. 4 shows results from the LC-Mass analysis in Example 1, showing the structure of the complex of the catalyst and the intermediate.

Furthermore, as shown in FIG. 4, 4-cyanocyclohexane carboxylic acid and/or a carboxylate anion thereof also seems to effect the dissolved state of the catalyst. Therefore, 4-cyanocyclohexane carboxylic acid and/or a carboxylate anion thereof may be quantified by an analysis method (for example, ion chromatography) so as to keep the amount to be 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 times equivalent or more to the total amount of the metal oxide and the metal salt in the reaction system, which may also be an effective method for reducing/suppressing precipitation of the catalyst. Moreover, the upper limit of the amount of 4-cyanocyclohexane carboxylic acid and/or a carboxylate anion thereof is preferably 150 times equivalent or less, and more preferably 100 equivalent or less. While the number and timing of the quantification are not particularly limited, quantification may take place, for example, every 10, 15, 20, 30, 40 or 50 minutes or every 1, 2, 3 or 4 hours. Moreover, the timing of the quantification may be altered during the reaction according to the progress of the reaction. For example, quantification may be conducted every 1 hour for the first 3 hours from the start of the reaction, and every 15 minutes thereafter. For example, the amount of 4-cyanocyclohexane carboxylic acid and/or a carboxylate anion thereof can be quantified by ion chromatography using a commercially available ion chromatograph (for example, ICS2000 available from Dionex Japan).

In the cyanation step of the present invention, the ammonia source may be obtained from ammonia (gas), urea, ammonium hydrogen carbonate, ammonium carbonate or a heated concentrate of an aqueous ammonia solution of aliphatic dicarboxylic acid. The mole ratio of the ammonia source and the aliphatic dicarboxylic acid used in the cyanation step (number of moles of ammonia source/number of moles of aliphatic dicarboxylic acid) is in a range of preferably 0.1-5, more preferably 0.3-4 and particularly preferably 0.5-3. When gas such as ammonia gas is used as the ammonia source, number of moles in the total flow rate per hour is assumed as the number of moles of the above-described ammonia source. When a heated concentrate of an aqueous ammonia solution of aliphatic dicarboxylic acid is used as the ammonia source, the method may comprise a step of heating an aqueous ammonia solution of an aliphatic dicarboxylic acid (specifically, an aqueous ammonia solution containing an aliphatic dicarboxylic acid) prior to the cyanation step so as to at least partially remove water to obtain the above-described heated concentrate (hereinafter, also referred to as a "heat concentration step"), where this step and the following cyanation step may be carried out continuously. The concentration of the aliphatic dicarboxylic acid in the aqueous ammonia solution is preferably 25-50 mol % relative to 100 mol % ammonium. Moreover, in the heat concentration step, the concentration of ammonia in the early aqueous ammonia solution is preferably 0.1-10 mass % to the total amount of the aqueous ammonia solution. Furthermore, the temperature upon heating to obtain the heated concentrate is preferably 100° C.-200° C. under either normal or high pressure.

In the cyanation step, an aliphatic dicarboxylic acid and an ammonia source are first introduced into the reactor, and if necessary, a solvent and a catalyst are fed therein. If ammonia gas is used, it may be introduced during heating. Thereafter, the reactor is heated until a predetermined temperature is obtained inside the reactor, and cyanation is allowed while suitably introducing inert gas into the reactor to keep the pressure inside the reactor to lie in a certain range and stirring inside the reactor. Moreover, the pressure in the system can be adjusted by introducing ammonia gas which is one kind of ammonia source.

As the catalyst, a metal oxide and/or a metal salt used for general cyanation can be employed. Specifically, examples of the metal oxide include one or more kinds selected from the group consisting of zinc oxide, tin(II) oxide, tin(IV) oxide, iron(II) oxide and iron(III) oxide. Among them, zinc oxide, tin(II) oxide and iron(III) oxide are preferable from the viewpoint of allowing cyanation to proceed more effectively and more surely. Examples of the metal salt include one or more kinds selected from the group consisting of a carbonate, a carboxylate, a sulfate, a nitrate and a halide of zinc, tin and iron, and a hydrate thereof. One or more kinds of catalysts may be used alone or in combination. Furthermore, the amount of the catalyst used is preferably 0.5-20 mass % relative to 100 mass % aliphatic dicarboxylic acid. By using the catalyst in an amount within the above-mentioned range, the yield and the selectivity of the resulting dicyanoalkane can be improved.

The cyanation step may be carried out with or without a solvent. Preferably, a solvent having a boiling point of 600° C. or lower, more preferably a solvent having a boiling point of 500° C. or lower and still more preferably a solvent having a boiling point of 420° C. or lower is used. In addition, the boiling point of the solvent, which should be higher than the reaction temperature of cyanation, is preferably 250° C. or higher, more preferably 270° C. or higher and still more preferably 300° C. or higher. If the boiling point is 300° C. or higher, cyanation is likely to proceed smoothly while generation of impurities such as a trimer of dicyanocyclohexane is suppressed.

Examples of the solvent used in the cyanation step include aliphatic alkanes such as heptadecane, nonadecane and docosane; aliphatic alkenes such as heptadecene, nonadecene and docosene; aliphatic alkynes such as heptadecyne, nonadecyne and docosyne; alkylbenzenes such as undecylbenzene, tridecylbenzene and tetradecylbenzene; alkyl-substituted aromatics such as dialkylbenzene and alkyl naphthalene; amide compounds such as undecanamide, laurylamide and stearamide; nitrile compounds such as tetradecanenitrile, hexadecanenitrile, 2-naphtyl acetonitrile, stearonitrile, 1,6-dicyanohexane, 1,8-dicyanooctane, 1,2-dicyanocyclohexane, 1,3-dicyanocyclohexane and 1,4-dicyanocyclohexane; ethers such as 4-dibromophenyl ether; halogenated benzenes such as 1,2,4,5-tetrachloro-3-nitrobenzene and 4,4'-dichlorobenzophenone; and ketones such as 2-phenylacetophenone and anthraquinone; and triphenylmethane.

Among them, alkyl naphthalene, triphenylmethane, dicyanohexane, dicyanooctane, dicyanocyclohexane and the like are favorable in that they do not hinder the progress of cyanation. More preferably, a final product is preferably used as the solvent so that a step for separating the solvent and the generated aliphatic dinitrile can be omitted.

While the solvent may not be used or used in any amount in the cyanation step as long as the cyanation proceeds sufficiently, the amount of the solvent used, for example, is preferably 20 times or less, more preferably 0.01-10 times, still more preferably 0.05-5 times and particularly preferably 0.1-3 times the mass of the aliphatic dicarboxylic acid and/or a salt thereof.

The reaction temperature in the cyanation step is preferably 200-340° C., more preferably 230-330° C. and still more preferably 250-320° C. While the reaction pressure may be any of negative, normal or positive, it is in a range of preferably 0.001 MPa-10 MPa, more preferably 0.05 MPa-5 MPa and still more preferably 0.08 MPa-0.12 MPa, for example, under normal pressure (0.1 MPa). By adjusting the concentrations of the respective raw materials and the reaction conditions to lie in the above-mentioned ranges, the yield and the selectivity of the resulting dicyanoalkane can be improved.

The reaction time is not particularly limited as long as the amount of the above-described amide compound represented by General formula (1) is maintained at 0.010 times equivalent or more to the total amount of the metal oxide and the metal salt, and may suitably be selected according to the reaction scale.

If necessary, the resulting reaction solution containing dicyanoalkane may be distilled to collect dicyanoalkane (hereinafter, this step is also referred to as a "distillation step"). For example, in a case of 1,4-dicyanocyclohexane, distillation can take place by heating the bottom while cooling the top of the distillatory such that the pressure is 3.0 kPa-4.0 kPa and the temperature is 180-230° C. in the system, thereby allowing gas-liquid contact inside the distillator. Hence, dicyanoalkane can selectively be removed and collected from the top of the distillator.

2. Method for Producing Bis(Aminomethyl)Alkane

The production method of this embodiment may comprise a step of obtaining bis(aminomethyl)alkane by subjecting dicyanoalkane obtained as described above to hydrogenation (hereinafter, also referred to as the "amination step"). In the amination step, the cyano group (—CN) is converted into an aminomethyl group (—CH$_2$NH$_2$). Bis(aminomethyl) alkane is an alkane having two aminomethyl groups resulting from hydrogenation of the cyano groups, and, for example, has the following structure.

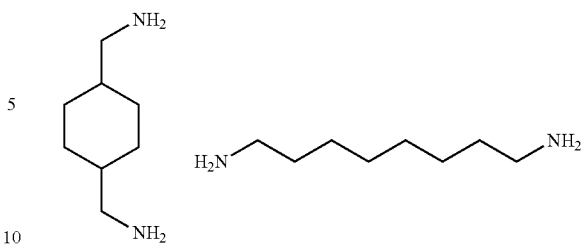

In the amination step, first, dicyanoalkane, a solvent and a catalyst are fed into the reactor, and then hydrogen gas is introduced until the pressure inside the system reaches a predetermined pressure. Thereafter, the reactor is heated until the temperature inside the reactor reaches the predetermined temperature and hydrogen gas is suitably introduced into the reactor such that the pressure inside the reactor is kept within a certain range to allow hydrogenation.

A solvent that is used in general hydrogenation may also be used as the solvent, where examples thereof specifically include alcohols such as methanol, ethanol, 1-propanol, 2-propanol, 1-butanol, 2-butanol and tert-butanol, aromatic hydrocarbons such as xylene, mesitylene and pseudocumene, liquid ammonia and ammonia water. One or more kinds of solvents can be used alone or in combination. Moreover, a catalyst that is used in general hydrogenation may also be used as the catalyst, where specific examples thereof include catalysts containing Ni and/or Co. In general, a catalyst that has Ni and/or Co supported on Al$_2$O$_3$, SiO$_2$, diatomite, SiO$_2$—Al$_2$O$_3$ or ZrO$_2$ by precipitation, Raney nickel or Raney cobalt can favorably be used as the catalyst. Among them, a Raney cobalt catalyst and a Raney nickel catalyst are preferable in that they can realize hydrogenation of nitrile more effectively and more surely. One or more kinds of catalysts may be used alone or in combination. Furthermore, the amount of catalyst used is preferably 0.1-150 mass %, more preferably 0.1-20 mass % and still more preferably 0.5-15 mass % relative to 100 mass % dicyanoalkane. By using the catalyst in an amount within the above-mentioned range, the yield and the selectivity of the resulting bis(aminomethyl)alkane can be improved.

The concentration of dicyanoalkane in the amination step is preferably 1-50 mass % and more preferably 2-40 mass % relative to the whole amount of the reaction solution for the sake of reaction efficiency. Moreover, the reaction temperature in the amination step is preferably 40-150° C. while the reaction pressure is preferably a hydrogen partial pressure of 0.5-15 MPa. Here, any reaction time can be employed as long as hydrogenation sufficiently proceeds. By adjusting the reaction conditions to lie in the above-mentioned ranges, the yield and the selectivity of the resulting bis(aminomethyl)alkane can be improved.

EXAMPLES

Hereinafter, the present invention will be described by means of examples, although the present invention should not be limited in any way to these examples.

Verification Example 1

100 g of 1,4-cyclohexane dicarboxylic acid (available from Tokyo Chemical Industry Co., Ltd.), 1.60 g of zinc oxide (available from Kanto Chemical Co., Inc.) and 100 g of 1,4-dicyanocyclohexane were fed into a 500-mL five-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised, and stirring was conducted at a reaction temperature of 300° C. for 6 hours. As a result, a precipitate was visually observed after 5 hours and 54 minutes. Change in the composition ratio of 1,4-dicyanocyclohexane and 4-cyanocyclohexane carboxamide before and after the precipitation of the catalyst was measured by gas chromatography (hereinafter, also referred to as GC). The results are shown in FIG. 1. GC was conducted under the same conditions as those described in Example 1 below. The amount of 4-cyanocyclohexane carboxamide after 6 hours of stirring was 1.7 mmol.

Example 1

Figure 2:
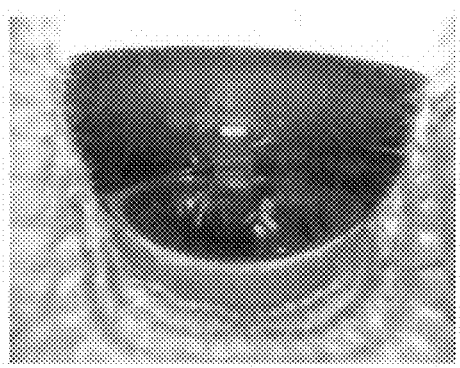
FIG. 2 is a picture showing the state of the reaction solution at the end of the reaction in Example 1.

100 g of 1,4-cyclohexane dicarboxylic acid (available from Tokyo Chemical Industry Co., Ltd.), 1.60 g of zinc oxide (available from Kanto Chemical Co., Inc.) and 100 g of 1,4-dicyanocyclohexane were fed into a 500-mL five-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised and stirring was continued at a reaction temperature of 300° C. A minute amount of the reaction solution was collected every hour for the first 4 hours following the start of the reaction and every 10 minutes thereafter, which was cooled to room temperature and then dissolved in methanol to be subjected to GC analysis. The amount of 4-cyanocyclohexane carboxamide after 5 hours of stirring was 3.8 mmol and about 0.19 times equivalent to the added zinc oxide (19.6 mmol), and thus the reaction was ended. At this point, no precipitate was visually observed in the reaction solution as can be appreciated from FIG. 2.

After the reaction, the reaction system was left to cool to room temperature, and the reaction product was dissolved in methanol to be subjected to GC analysis. As a result, the conversion rate of 1,4-cyclohexanedicarboxylic acid was 99.9% while the yield of 1,4-dicyanocyclohexane was 89.0%. The yield here does not contain the fed 1,4-dicyanocyclohexane, which also applies to the yields in the examples and the comparative examples described hereinbelow. Furthermore, LC-Mass analysis of the reaction solution at this point showed that a complex of 1 equivalent of zinc and 3 equivalents of 4-cyanocyclohexane carboxylic acid was observed (see FIG. 4). Moreover, ICP analysis showed that the precipitated zinc was 3.1 wt % relative to the zinc contained in the added zinc oxide. GC, LC-Mass and ICP analyses were conducted under the following conditions. In addition, the reaction solution at the end of the reaction in Example 1 was analyzed using an ion chromatograph (ICS2000 available from Dionex Japan, eluate: an aqueous solution of KOH, column: AS17C). As a result, the carboxylate anion of 4-cyanocyclohexane carboxylic acid was 1.0 time equivalent to zinc oxide.

<Conditions for GC Analysis>

Analyzer: Product type "GC2010 PLUS" available from Shimadzu Corporation

Column: Product name "HP-5 ms" (available from Agilent Technologies Japan, Ltd., length 30 m×inner diameter 0.25 mm, film thickness 0.25 μm)

Carrier gas: He (constant pressure: 73.9 kPa)

Inlet temperature: 300° C.

Detector: FID

Temperature of detector: 300° C.

Temperature of column oven: starting at 100° C., heated to 300° C. at 10° C./min and kept at 300° C. for 30 minutes <Conditions for LC-Mass Analysis>

Instrument and conditions for HPLC analysis

Instrument: U3000 Rapid Separation LC (available from Thermo Fisher Scientific)

Column: None (flow injection)

Temperature: 35° C.

Mobile liquid, flow rate: acetonitrile, 0.2 ml/min

Sample concentration, injected amount: 15-fold dilution, 10 μL

Detector: PDA (wavelength of extraction 254 nm)

Instrument and conditions for MS analysis

Instrument: LTQ Orbitrap Discovery (available from Thermo Fisher Scientific)

Ionization: ESI negative ion mode

<Conditions for ICP-AES Analysis>

Analyzer: ICP optical emission spectrometer (Vista-PRO Axial available from Agilent Technologies Japan, Ltd.)

The amount of precipitated zinc (wt %) was measured by the following method. 4.0 g of the reaction product obtained in Example 1 was weighed, to which methanol (20 ml) was added to perform ultrasonic dissolution for 15 minutes. Pressure filtration was conducted with a membrane filter (ADVANTEC (registered trademark) H100A047A), and the resultant was washed with methanol (30 ml) and dried. To the resulting residue, an aqueous 0.1M nitric acid solution was added to carry out wet digestion. A solution obtained by diluting the resultant with ultrapure water was analyzed by ICP-AES.

Comparative Example 1

Figure 3:
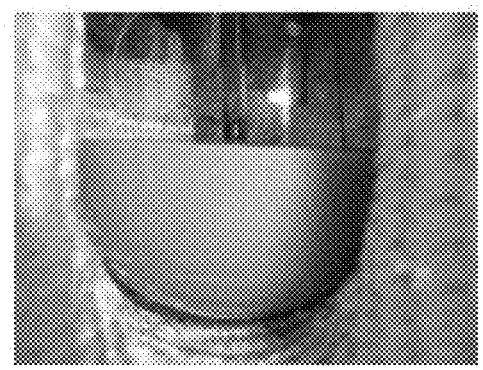
FIG. 3 is a picture showing the state of the reaction solution at the end of the reaction in Comparative example 1.

Similar to Example 1, 100 g of 1,4-cyclohexanedicarboxylic acid, 1.60 g of zinc oxide and 100 g of 1,4-dicyanocyclohexane were fed into a 500-mL five-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised, and stirring was conducted at a reaction temperature of 300° C. for 6 hours. As a result, a precipitate was visually observed as can be appreciated from FIG. 3.

After the reaction, the reaction product was dissolved in methanol, and the precipitate was separated by conducting pressure filtration with a membrane filter (ADVANTEC (registered trademark) H100A047A) so as to analyze the filtrate by GC. As a result, the conversion rate of 1,4- cyclohexanedicarboxylic acid was 99.9% while the yield of 1,4-dicyanocyclohexane was 89.9%. Moreover, the content of 4-cyanocyclohexane carboxamide was 0.18 mmol, which was 0.009 times equivalent to the added zinc oxide (19.6 mmol). ICP analysis of the residue obtained upon the above-described pressure filtration found that the precipitated zinc was 81.0 wt % relative to zinc of the added zinc oxide.

<Conditions for ICP-AES Analysis>

An aqueous 0.1M nitric acid solution was added to the above-described residue to perform wet digestion, and a solution obtained by diluting the resultant with ultrapure water was analyzed by ICP-AES.

Example 2

100 g of 1,4-cyclohexanedicarboxylic acid, 1.32 g of tin(II) oxide (available from Wako Pure Chemical Industries, Ltd.) and 100 g of 1,4-dicyanocyclohexane were fed into a 500-mL three-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised and stirring was continued at a reaction temperature of 300° C. A minute amount of the reaction solution was appropriately collected, left to cool to room temperature and dissolved in methanol to be analyzed by GC. After 4 hours and 30 minutes of stirring, the amount of 4-cyanocyclohexane carboxamide became 8.3 mmol and 0.85 times equivalent to the amount of the catalyst (9.8 mmol), and thus the reaction was ended. At this point, no black precipitate of tin oxide was visually observed in the reaction solution.

After the reaction, the reaction system was left to cool to room temperature, and the reaction product was dissolved in methanol to be analyzed by GC. As a result, the conversion rate of 1,4-cyclohexanedicarboxylic acid was 99.9% while the yield of 1,4-dicyanocyclohexane was 87.3%. Furthermore, the reaction solution was analyzed by ICP in the same manner as Example 1. As a result, the precipitated tin was 5.1 wt % relative to tin contained in the added tin oxide.

Comparative Example 2

100 g of 1,4-cyclohexanedicarboxylic acid, 1.32 g of tin(II) oxide and 100 g of 1,4-dicyanocyclohexane were fed into a 500-mL three-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised and stirring was conducted at a reaction temperature of 300° C. for 6 hours, whereby the reaction was terminated. At this point, a precipitate was visually observed in the reaction solution.

After the reaction, the reaction system was left to cool to room temperature. The reaction product was dissolved in methanol and subjected to pressure filtration with membrane filter to separate the precipitate. The filtrate was analyzed by GC. As a result, the conversion rate of 1,4-cyclohexanedicarboxylic acid was 99.9% while the yield of 1,4-dicyanocyclohexane was 88.6%. Moreover, the content of 4-cyanocyclohexane carboxamide was 0.08 mmol and 0.008 times equivalent to the added tin oxide (9.8 mmol). The residue upon pressure filtration was subjected to the same treatment as Comparative example 1 to be analyzed by ICP. As a result, the precipitated tin was 78.5 wt % to tin contained in the added tin oxide.

Example 3

100 g of 1,4-cyclohexanedicarboxylic acid, 0.78 g of $Fe_2O_3$ (III) (available from Wako Pure Chemical Industries, Ltd.) and 100 g of 1,4-dicyanocyclohexane were fed into a 500-mL five-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised and stirring was continued at a reaction temperature of 300° C. A minute amount of the reaction solution was appropriately collected, left to cool to room temperature and dissolved in methanol to be analyzed by GC. After 4 hours and 30 minutes of stirring, the amount of 4-cyanocyclohexane carboxamide became 7.3 mmol and about 0.74 times equivalent to the added iron ion (9.8 mmol), and thus the reaction was ended.

After the reaction, the reaction system was left to cool to room temperature, and the reaction product was dissolved in methanol to be analyzed by GC. As a result, the conversion rate of 1,4-cyclohexanedicarboxylic acid was 99.9% while the yield of 1,4-dicyanocyclohexane was 91.1%. In addition, the reaction solution was analyzed by ICP in the same manner as Example 1. As a result, the precipitated iron was 54.7 wt % relative to iron contained in the added iron oxide.

Comparative Example 3

100 g of 1,4-cyclohexanedicarboxylic acid, 0.78 g of $Fe_2O_3$ (III) and 100 g of 1,4-dicyanocyclohexane were fed into a 500-mL five-neck flask equipped with a stirring blade, a gas supply pipe that allows adjustment of the supplying height, a thermocouple and a dehydrator. Nitrogen gas (supply rate 68 ml/min) and ammonia gas (supply rate 348 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised and stirring was conducted at a reaction temperature of 300° C. for 6 hours, whereby the reaction was terminated. At this point, a precipitate was visually observed in the reaction solution.

After the reaction, the reaction system was cooled to room temperature. The reaction product was dissolved in methanol and subjected to pressure filtration with membrane filter to separate the precipitate. The filtrate was analyzed by GC. As a result, the conversion rate of 1,4-cyclohexanedicarboxylic acid was 99.9% while the yield of 1,4-dicyanocyclohexane was 92.3%. Moreover, the content of 4-cyanocyclohexane carboxamide was 0.06 mmol and 0.006 times equivalent to the added iron ion (9.8 mmol). The residue upon pressure filtration was subjected to the same treatment as Comparative example 1 to be analyzed by ICP. As a result, the precipitated iron was 95.8 wt % relative to the iron contained in the added iron oxide.

Example 4

(Production of Bis(Aminomethyl)Cyclohexane)

24.4 g of 1,4-dicyanocyclohexane, 37.3 g of methanol and 28.4 g of 28% ammonia water (available from Wako Pure Chemical Industries, Ltd.) as a solvent, and 0.56 g of Raney cobalt catalyst (available from Wako Pure Chemical Industries, Ltd.) as a catalyst were fed into a 300-mL SUS316-made pressure resistant container, and hydrogen gas was introduced into the container until reaction pressure of 4.5 MPa was reached. Subsequently, the container was heated until the temperature inside reached the reaction temperature of 80° C., whereby the temperature was kept constant to allow amination (nitrile hydrogenation) via hydrogenation for 240 minutes while stirring inside the container with a magnetic stirring blade at 750 rpm. As a result, the conversion rate of 1,4-dicyanocyclohexane was 100% while the selectivity and the yield of 1,4-bi s(aminomethyl)cyclohexane were 97.0% and 97.0%, respectively.

Example 5

(Production of Suberonitrile)

20 g of suberic acid (available from Tokyo Chemical Industry Co., Ltd.), 317 mg of zinc oxide and 20 g of suberonitrile (available from Tokyo Chemical Industry Co., Ltd.) were fed into a 100-mL three-neck flask equipped with a stirring blade, a gas supply pipe that allows adjustment of the supplying height, a thermocouple and a dehydrator. Nitrogen gas (supply rate 20 ml/min) and ammonia gas (supply rate 70 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. Stirring was continued at a reaction temperature in a range of 260-270° C. A minute amount of the reaction solution was appropriately collected, left to cool to room temperature and dissolved in methanol to be analyzed by GC. After 6.5 hours of stirring, the amount of 7-cyanoheptaneamide became 3.2 mmol and 0.82 times equivalent to the amount of the catalyst (3.9 mmol), and thus the reaction was ended. At this point, no precipitate was visually observed in the reaction solution.

After the reaction, the reaction system was left to cool to room temperature, and the reaction product was dissolved in methanol to be analyzed by GC. As a result, the yield of suberonitrile without the fed suberonitrile was 49.7%. In addition, when the reaction solution was analyzed by ICP in the same manner as Example 1, the precipitated zinc was 58.5 wt % to zinc contained in the added zinc oxide.

Comparative Example 4

20 g of suberic acid, 317 mg of zinc oxide and 20 g of suberonitrile were fed into a 100-mL three-neck flask equipped with a stirring blade, a gas supply pipe that allows adjustment of the supplying height, a thermocouple and a dehydrator. Nitrogen gas (supply rate 20 ml/min) and ammonia gas (supply rate 70 ml/min) were introduced into the flask via the gas supply pipe provided above the liquid surface at 170° C. while stirring at 300 rpm. Once the temperature of the reaction system reached 270° C., the gas supply port was descended into the reaction solution to initiate bubbling, which was considered the start of cyanation. The temperature of the reaction system was further raised and stirring was continued at a reaction temperature of 300° C. for 7 hours. At this point, a precipitate was visually observed in the reaction solution.

After the reaction, the reaction system was left to cool to room temperature. The reaction product was dissolved in methanol, and the precipitate was separated by performing pressure filtration with a membrane filter. The filtrate was analyzed by GC. As a result, the yield of suberonitrile without the fed suberonitrile was 39.4%. In addition, 7-cyanoheptaneamide was not detected by GC analysis. When the residue upon pressure filtration was subjected to the same treatment as Comparative example 1 to be analyzed by ICP, the precipitated zinc was 73.0 wt % relative to zinc contained in the added zinc oxide.

Example 6

(Production of 1,8-Diaminooctane)

A stirring bar, 1.0 g of suberonitrile, 1.6 g of ethanol, 1.1 g of 28% ammonia water and 0.1 g of a Raney cobalt catalyst as a catalyst were fed into a 30-mL SUS316-made pressure resistant container equipped with a stirring bar, and hydrogen gas was introduced into the container until reaction pressure of 8.7 MPa was reached. Subsequently, the container was heated until the temperature inside reached the reaction temperature of 80° C., whereby the temperature was kept constant to allow amination via hydrogenation for 60 minutes while stirring inside the container with a magnetic stirrer at 600 rpm. As a result, the conversion rate of suberonitrile was 100% while the yield of 1,8-diaminooctane was 90.2%.

The invention claimed is:

1. A method for producing a dicyanoalkane, comprising:
cyanating one or more aliphatic dicarboxylic acids and/or salts thereof with an ammonia source in the presence of a metal oxide and/or a metal salt and an amide compound comprising an amido alkane carboxylic acid, an alkane diamide, a cyanoalkane carboxamide, and/or derivative of any of these in which a hydrogen of the amide $NH_2$ is substituted with another heteroatom
wherein the alkane of the amide and/or derivative is substituted or unsubstituted,
wherein, in the cyanating, an amount of the amide compound and/or derivative is maintained at 0.010 times equivalent or more to a total amount of the metal oxide and the metal salt after an amount of the amide compound and/or derivative becomes 0.010 times equivalent or more relative to a total amount of the metal oxide and the metal salt after starting the cyanating, and
wherein the amount of the amide compound and/or derivative is quantified during the cyanating.

2. The method of claim 1, wherein the ammonia source is ammonia, urea, ammonium hydrogen carbonate, ammonium carbonate, or a heated concentrate of an aqueous solution of an ammonium salt of an aliphatic dicarboxylic acid.

3. The method of claim 1, wherein the amide compound and/or derivative comprises the amido alkane carboxylic acid.

4. The method of claim 1, wherein the metal oxide comprises zinc oxide, tin oxide, and/or iron oxide.

5. The method of claim 1, wherein the metal salt comprises a carbonate, a carboxylate, a sulfate, a nitrate, a halide, and/or a hydrate thereof.

6. The method of claim 1, wherein the amount of the amide compound and/or derivative is maintained at 0.010 times equivalent or more to the total amount of the metal oxide and the metal salt by adding the amide compound and/or derivative thereof during the cyanating.

7. The method of claim 1, wherein the cyanating is ended before the amount of the amide compound and/or derivative becomes less than 0.010 times equivalent to the total amount of the metal oxide and the metal salt.

8. A method for producing a diaminoalkane, the method comprising:
    producing a dicyanoalkane by the method of claim 1; and
    hydrogenating the dicyanoalkane to obtain a bis(aminomethyl)alkane.

9. The method of claim 1, wherein the alkane in the amide compound and/or derivative is an unsubstituted hydrocarbon group.

10. The method of claim 1, wherein the alkane in the amide compound and/or derivative is a substituted hydrocarbon group.

11. The method of claim 1, wherein the ammonia source is urea.

12. The method of claim 1, wherein the ammonia source is ammonium hydrogen carbonate.

13. The method of claim 1, wherein the ammonia source is an aqueous solution of an ammonium salt of an aliphatic dicarboxylic acid.

14. The method of claim 1, wherein quantification is carried out in a range of from every 10 minutes to every 3 hours.

15. A method for producing a dicyanoalkane, comprising:
    cyanating one or more aliphatic dicarboxylic acids and/or salts thereof with an ammonia source in the presence of a metal oxide and/or a metal salt and an amide compound comprising an amido alkane carboxylic acid, an alkane diamide, a cyanoalkane carboxamide, and/or derivative of any of these in which a hydrogen of the amide $NH_2$ is substituted with another heteroatom
    wherein the alkane of the amide and/or derivative is substituted or unsubstituted, and
    wherein, in the cyanating, an amount of the amide compound and/or derivative is maintained at 0.010 times equivalent or more to a total amount of the metal oxide and the metal salt after an amount of the amide compound and/or derivative becomes 0.010 times equivalent or more relative to a total amount of the metal oxide and the metal salt after starting the cyanating.

16. The method of claim 15, wherein the amide compound is at least one selected from the group consisting of an amido alkane carboxylic acid, an alkane diamide, and a cyanoalkane carboxamide.

17. The method of claim 1, wherein the amide compound comprises the alkane diamide.

18. The method of claim 1, wherein the amide compound comprises the cyanoalkane carboxamide.

19. The method of claim 1, wherein the amide compound comprises the alkane diamide and the cyanoalkane carboxamide.

20. The method of claim 1, wherein the amide compound comprises the amido alkane carboxylic acid and the cyanoalkane carboxamide.

* * * * *